US008109875B2

(12) United States Patent
Gizewski (10) Patent No.: US 8,109,875 B2
(45) Date of Patent: Feb. 7, 2012

(54) DERMA DIAGNOSTIC AND AUTOMATED DATA ANALYSIS SYSTEM

(76) Inventor: Theodore M. Gizewski, Santa Barbara, CA (US)

( * ) Notice: Subject to any disclaimer, the term of this patent is extended or adjusted under 35 U.S.C. 154(b) by 1260 days.

(21) Appl. No.: 11/649,921

(22) Filed: Jan. 3, 2007

(65) Prior Publication Data

US 2008/0161661 A1    Jul. 3, 2008

(51) Int. Cl.
*A61B 5/00* (2006.01)
(52) U.S. Cl. ........................ 600/306; 600/300
(58) Field of Classification Search ............... 600/300, 600/306
See application file for complete search history.

(56) References Cited

U.S. PATENT DOCUMENTS

| | | | |
|---|---|---|---|
| 5,785,960 A | 7/1998 | Rigg et al. | |
| 5,796,862 A | 8/1998 | Pawlicki et al. | |
| 5,836,872 A * | 11/1998 | Kenet et al. | 600/306 |
| 6,021,344 A * | 2/2000 | Lui et al. | 600/476 |
| 6,168,563 B1 * | 1/2001 | Brown | 600/301 |
| 6,571,003 B1 * | 5/2003 | Hillebrand et al. | 382/118 |
| 6,792,137 B2 * | 9/2004 | Kenet | 382/128 |
| 6,916,288 B2 * | 7/2005 | Nakata | 600/306 |
| 6,937,749 B2 * | 8/2005 | Garnier | 382/128 |
| 7,233,693 B2 | 6/2007 | Momma | |
| 7,454,046 B2 | 11/2008 | Chhibber et al. | |
| 7,477,767 B2 * | 1/2009 | Chhibber et al. | 382/128 |
| 7,738,032 B2 * | 6/2010 | Kollias et al. | 348/370 |
| 7,856,118 B2 * | 12/2010 | Kalla et al. | 382/100 |
| 2003/0065523 A1 * | 4/2003 | Pruche et al. | 705/1 |
| 2004/0125996 A1 * | 7/2004 | Eddowes et al. | 382/128 |
| 2004/0215066 A1 * | 10/2004 | Huang et al. | 600/300 |
| 2006/0095297 A1 * | 5/2006 | Virik | 705/2 |
| 2006/0111620 A1 * | 5/2006 | Squilla et al. | 600/300 |
| 2007/0040907 A1 * | 2/2007 | Kern et al. | 348/77 |
| 2007/0125390 A1 * | 6/2007 | Afriat et al. | 128/898 |
| 2007/0179361 A1 * | 8/2007 | Brown et al. | 600/300 |
| 2007/0225578 A1 * | 9/2007 | Howell et al. | 600/306 |
| 2008/0051638 A1 * | 2/2008 | Iliff | 600/300 |
| 2008/0147053 A1 * | 6/2008 | Kang et al. | 606/9 |
| 2008/0275315 A1 * | 11/2008 | Oka et al. | 600/306 |
| 2009/0118600 A1 * | 5/2009 | Ortiz et al. | 600/306 |
| 2009/0326383 A1 * | 12/2009 | Barnes et al. | 600/476 |
| 2010/0185064 A1 * | 7/2010 | Bandic et al. | 600/306 |
| 2010/0218118 A1 * | 8/2010 | Bronkema | 715/751 |
| 2011/0215930 A1 * | 9/2011 | Lee et al. | 340/573.1 |
| 2011/0301441 A1 * | 12/2011 | Bandic et al. | 600/306 |

OTHER PUBLICATIONS

Automatic Quantitative Analysis of Healing Skin Wounds using Colour Digital Image Processing, WP Berriss, SJ Sangwine, World Wide Wounds, Sep. 1997, edition 1.1.*

* cited by examiner

*Primary Examiner* — Miranda Le
*Assistant Examiner* — Karen Toth
(74) *Attorney, Agent, or Firm* — Guy L. Cumberbatch (57) ABSTRACT

Disclosed is a derma diagnostic and automated data analysis system configured to acquire an array of data pertaining to a subject and their skin disorders. This data is subjected to a comprehensive analysis that culminates in diagnoses, treatments, monitoring activity and health strategy implementation. The derma diagnostic and automated data analysis system comprises a user interface and display unit, capable of acquiring a range of subject data, and communicatively coupled to a remotely located data analysis and reporting unit. The data analysis and reporting unit is capable of receiving and assessing the acquired data, using multiple analytical processes that culminate in a highly probable diagnosis and an effective treatment that is documented in a report and submitted to the subject. The diagnoses, treatments and supporting data are then permanently archived and made available for retrieval.

34 Claims, 5 Drawing Sheets

DERMA DIAGNOSTIC AND AUTOMATED DATA ANALYSIS SYSTEM

FIELD OF THE INVENTION

The present invention generally relates to a health maintenance system, and more particularly, relates to a derma diagnostic and automated data analysis system for diagnosing the nature, probable cause, progression, severity, treatment and monitoring of both common and exotic derma or skin abnormalities affecting humans and animals.

BACKGROUND OF THE INVENTION

Innumerable people, worldwide, suffer from skin disorders. These skin disorders can include burns, cuts, sores, dry skin, thinning skin, wrinkling, eczema, inflammations, itchy skin, infections, psoriasis, skin rashes, sunburn, parasites and many more. The reasons for these skin problems may be faulty diet, hormone imbalances, blood toxicity, ineffective cleansing, illness, disease, injury, exposure to an irritants or caustic substances, allergies, aging, excess or improper use of cosmetics or any other reason, causing an afflicted individual or subject discomfort or suffering. To relieve this suffering, the afflicted individual or subject needs to pursue: (1) a quick and accurate diagnosis; (2) identification and administration of an effective treatment; (3) monitoring the progression of the condition and the effectiveness of the treatment; (4) identify and implement of prevention, avoidance and/or mitigation strategies; and (5) long term surveillance.

In a traditional outpatient consultation and treatment process, the subject observes or is in some way made aware of a skin condition or disorder which causes him/her to consult with a physician. The physician asks a series of questions and does a preliminary examination. On conformation of a skin condition or disorder, the physician refers the subject to a specialist, typically a dermatologist, wherein a second appointment is made and the subject proceeds to consult with the dermatologist. The dermatologist reviews the referring physician's notes and asks a series of additional questions, many of which are the same as those asked by the referring physician. The dermatologist then performs an examination and may surgically or in some other way remove a sample of tissue for closer examination under a microscope or by a laboratory. It is also likely that, if laboratory testing is prescribed, a select set of blood tests will also be ordered. This will require the subject to schedule a third appointment to address the lab work. Several days or weeks after the visit to the lab, the subject is given a follow-up appointment with the dermatologist who: reviews his/her notes from the previous visit; reviews the lab reports; asks a few more questions; and reexamines the affected area. If the medical history, symptoms and lab results point to a skin condition or disorder that the dermatologist is familiar with, the dermatologist will make a diagnosis and prescribe a treatment. On the other hand, if the dermatologist does not recognize the symptoms, the dermatologist will order additional laboratory tests and may consult with another specialist. This process will continue until a diagnosis can be made or until no specific diagnosis can be made (based on the resources available to the dermatologist) and the condition/disorder is labeled as a non-specific disorder and a treatment may be prescribed to address one or more of the overt symptoms.

When a condition is unchanged or worsens, due to a misdiagnosis or failure-to-diagnose situation, the appointment, questioning, examination and lab work sequence is resumed until the next diagnosis and treatment. This process is inherently flawed due to its highly qualitative nature, requiring human judgment, experience, training/education, knowledge, curiosity, intuition, skill, interest, energy, memory, motivation, intelligence and many other variable and often limited human characteristics. Consequentially, serious problems such as misdiagnosis, delayed-diagnosis, failure-to-diagnose and failure-to-detect treatment complications occur more frequently than what is desired or appropriate. This process is also inefficient and expensive, requiring: access to qualified physicians; a protracted period of time to acquire a diagnosis; a significant amount of high-cost physician labor hours; and unnecessary laboratory tests.

In recent time, technology and medical science has shown significant developments in this field of detecting, diagnosing, and treating derma disorders. Derma disorders can display unique visible spectrum, fluorescent, and radiometric characteristics, thus attempts have been made wherein by digitally capturing the quantitative value of theses characteristics of a derma disorder, analysis may be performed. Derma disorder analysis and condition diagnosis may be done by local or remotely situated dermatologists by looking at these captured quantitative values. Attempts could be seen wherein computerized systems have been used to address some of the derma disorders.

U.S. Pat. No. 6,571,003 discloses an apparatus and method that can be implemented by a human operator and a computing device to analyze and display human skin images. The system acquires a digital image from a camera or scanner. Subsequently, the system determines which area(s) of the image to analyze using landmarks such as the corner of the eye. The determined areas are then analyzed to locate skin defects such as red spots, and the defects are visually identified on a display. A severity is calculated for the defects and the severity is compared to an average skin severity associated with a population of people. In addition, a simulation is generated and displayed showing an improvement to the defect areas. The above approach is limited to solve the visual skin problems of a subject's face and enables a beauty counselor in selecting a suitable cosmetic product in regard to the subject's facial problem.

United States Patent Publication Number 20060095297 discloses a kiosk for topical skin assessment surveys and skin care selection. The topical skin assessment survey is performed by a self-guided interactive program using a plurality of UVA lamps which illuminate trouble spots on the skin that cannot be seen in a natural light environment. The kiosk also provides price comparison of available cosmetic and skincare products, and the option to purchase products. The above approach simply enables a subject to select a suitable cosmetic product present in kiosk database, and the equipment used for analysis dose not includes advance technologies and methodologies.

Such attempts have addressed only a miniscule portion of the derma problems at large. Accordingly, what is needed is a comprehensive, automated derma diagnostic system for assessing the condition of a subject's skin or derma, in order to establish a diagnosis, prescribe a treatment and monitor a condition's progression and the effectiveness of the treatment.

SUMMARY OF THE INVENTION

The general purpose of the present invention is to provide a readily accessible, highly effective, automated derma detection, analysis, diagnostic, treatment, and monitoring system which is capable of detecting the presence of a derma disorder and assessing the: nature; circumstances; probable cause;

progression; and severity of common and exotic derma conditions, injuries and disorders that affect humans and animals. Also incorporated, into the present invention, is the capability of systematically monitoring the stages of a derma condition and monitoring the effectiveness of a prescribed treatment. The present invention would include the advantages of the prior art and overcome the drawbacks inherent therein.

In one aspect, the present invention provides a derma diagnostic and automated data analysis system. The derma diagnostic and automated data analysis system comprises at least one user interface and display unit capable of interacting with a subject and acquiring subject data from the subject, and at least one data analysis and reporting unit communicatively coupled to the user interface and display unit. The data analysis and reporting unit is capable of remotely controlling the interactions between the user interface and display unit and the subject, and acquiring and analyzing subject data for developing diagnosis, prescribing treatments, initiating monitoring processes, prescribing health strategies, generating health reports, and archiving diagnoses and treatments.

In another aspect, the present invention provides a method of performing automated data analysis for diagnosing skin disorders of a subject and prescribing treatments. The method comprises: acquiring preliminary subject information, including descriptive data, background data and a description of skin condition, using user-interface features of a user interface and display unit; transmitting the acquired preliminary subject information to a data analysis and reporting unit over a communication network; processing preliminary subject information for establishing a data acquisition strategy which is implemented through the user interface and display unit by user interface and display unit; systematically acquiring supportive data and skin condition imagery, sensory, and test and measurement data based on the established data acquisition strategy by user interface and display unit; analyzing the data and developing primary and secondary diagnoses and treatments by data analysis and reporting unit, monitoring criteria, and health strategies; generating a series of health status reports incorporating diagnoses, treatments, monitoring criteria, and health strategies which are transmitted to the user interface and display unit over the communication network by data analysis and reporting unit; and user interface and display unit acting to present the health status reports to the subject.

These, together with other aspects of the present invention, along with the various features of novelty that characterize the invention, are pointed out with particularity in the claims annexed hereto and forming a part of this disclosure. For a better understanding of the invention, its operating advantages, and the specific objects attained by its uses, reference should be made to the accompanying drawings and descriptive matter in which there are illustrated exemplary embodiments of the invention.

BRIEF DESCRIPTION OF THE DRAWINGS

The advantages and features of the present invention will become better understood with reference to the following more detailed description and claims taken in conjunction with the accompanying drawings, wherein:

Like reference numerals refer to like parts throughout several views of the drawings of the present invention.

DETAILED DESCRIPTION OF THE INVENTION

For a thorough understanding of the subject invention, reference is to be made to the following detailed description, including the appended claims, in connection with the above-referenced drawings. Although, the present invention is described in connection with several embodiments, the invention is not intended to be limited to the specific forms set forth herein. On the contrary, it is intended to cover such alternatives, modifications, and equivalents as can be reasonably included within the scope of the invention as defined by the appended claims.

In the following description, for purposes of explanation, numerous specific details are set forth in order to provide a thorough understanding of the invention. It will be apparent, however, to one skilled in the art that the invention may be practiced without these specific details.

The present invention provides a derma diagnostic and automated data analysis system for a readily available, efficient and economical method of detecting, analyzing, diagnosing, treating and monitoring both common and exotic derma abnormalities/diseases/infections/conditions/disorders/injuries (herein cumulatively referred to as abnormalities or disorders) that affect humans and animals. The derma diagnostic and automated data analysis system utilizes multiple abnormality detection technologies to sense and image skin disorders for capturing a significant number of different kinds of skin disorder characteristics and further cross-checking against each other and authoritative standards for ensuring consistency and a higher confidence in diagnosis. The derma diagnostic and automated data analysis system, of the present invention, acquires imagery, sensory, test and measurement, and supportive data as quantitative values. The imagery and sensory data may be acquired from multiple devices, utilizing different technologies. This information is then transmitted over a communication network, to a remotely situated repository for analysis and generating reports. The quantitative values are then processed and analyzed in order to form a diagnosis, develop treatment options, construct monitoring programs and develop personalized health strategies. A detailed report is generated and thereafter transmitted, over the communication network and presented to the subject.

'Subject', as used in this specification, refers to afflicted individuals, and users subscribing to or using the derma diagnostic and automated data analysis system for the purposes of detecting, diagnosing, treating and monitoring both common and exotic derma conditions, abnormalities and disorders.

The imagery, sensory, and supportive data, acquired from the subject, may be hereinafter referred to for the purposes of explanation as 'subject data'. The subject data may be captured through a series of inquiries and diagnostic tests.

Figure 1:
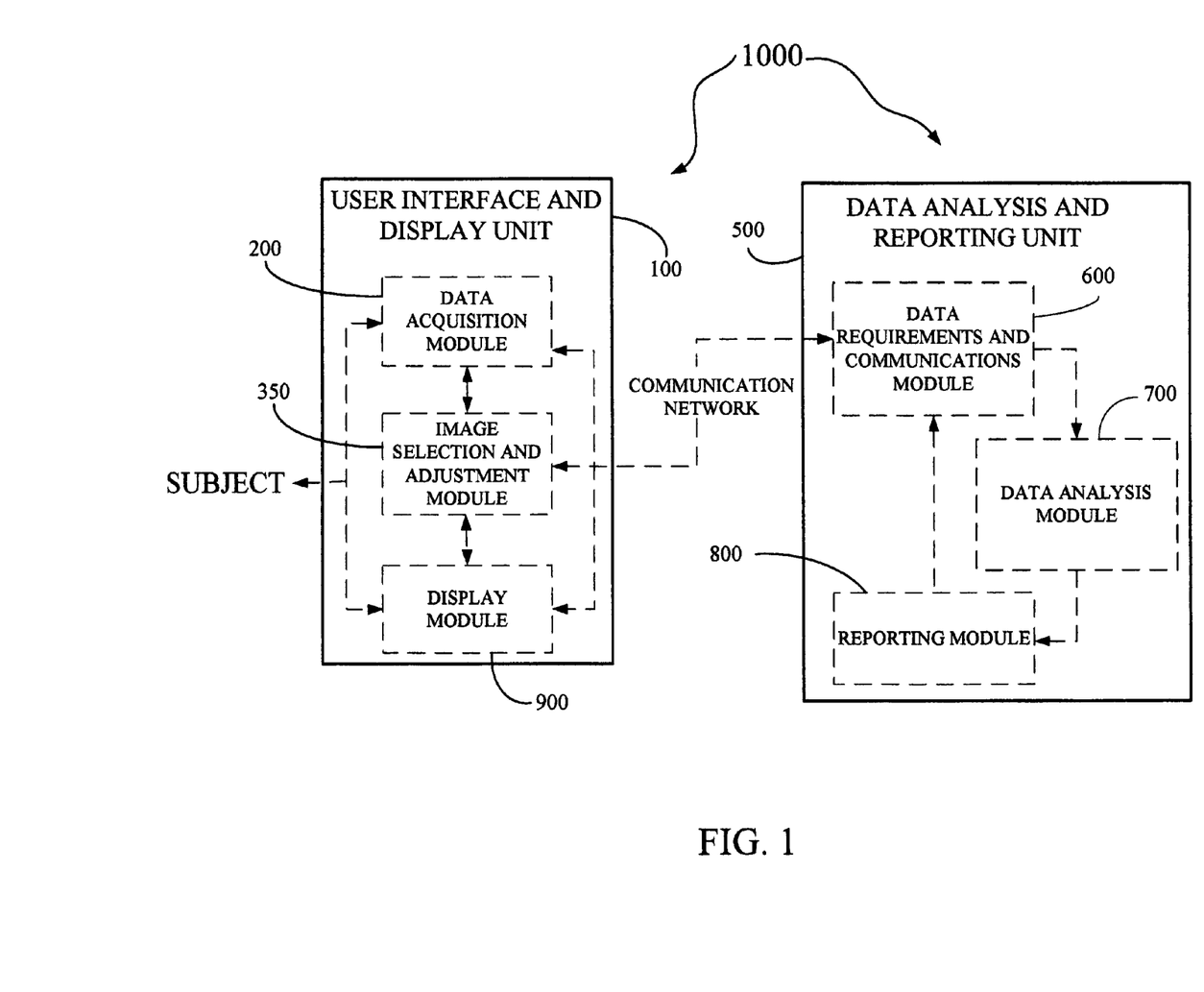
FIG. 1 is a block diagram illustrating derma diagnostic and automated data analysis system 1000, according to an exemplary embodiment of the present invention.

Referring to FIG. 1, illustrated is one exemplary embodiment of a derma diagnostic and automated data analysis system 1000 of the present invention (hereinafter, referred to as 'system' 1000). The system 1000 may comprise a user interface and display unit 100, communicatively coupled to a data analysis and reporting unit 500, through a communication network, for example, the Internet. Alternatively, the communication network may include a public switched telephone network (PSTN), global system for mobile communications (GSM) network, general packet radio service (GPRS) network, and the like, to establish communication between the user interface and display unit 100 and the data analysis and reporting unit 500. The user interface and display unit 100 configuration may include a data acquisition module 200, an image selection and adjustment module 350, and a display module 900. The data acquisition module 200 may be responsible for acquiring quantitative subject data including an array of imagery, sensory, test and measurement data, as well as supportive data that addresses the subject's particular characteristics and the particular characteristics of the skin condition, abnormality or disorder. Further, the data analysis and reporting unit 500 may be configured to comprise a data requirements and communications module 600, a data analysis module 700 and a reporting module 800. The user interface features of the user interface and display unit 100, or more specifically, the features of the data acquisition module 200, the image selection and adjustment module 350, and the display module 900 may include or support audio communication features, video communication features, data security features, and the like, for implementing sophisticated graphical-user-interface technologies, enhanced audio and voice recognition facilities for advanced data security features. The user interface features may interact with the subject at a personal level, very much the way a person would interact with a trusted advisor rather than the rigid and regimented way people typically interact with computers.

The subject data, collected by the data acquisition module 200 may be transmitted, through the communication network, to the data analysis and reporting unit 500 wherein the data requirements and communications module 600 receives, organizes, structures, and prepares the investigatory subject data as subject data elements which may then be submitted to the data analysis module 700 for analysis. The data analysis module 700 applies a plurality of analytical processes which may be based on specific programmable instructions that address analytical protocols and include data structuring, the establishment of relative and absolute relationships between the subject data elements themselves and between the subject data elements and specially compiled databases containing authoritative standards and reference materials. The user interface and display unit 100 maybe designed to capture a variety of particular characteristics of a condition or disorder, utilizing multiple and diverse technologies. Each variation of imagery data, sensory data, and test and measurement data may be systematically weighted and assessed. Upon completion of the analysis process, by the data analysis module 700, the analytical results are submitted to the reporting module 800 where it may prepare a series of reports which are submitted back to the data requirements and communications module 600 and finally to the subject through the display module 900 of the user interface and display unit 100.

Figure 2:
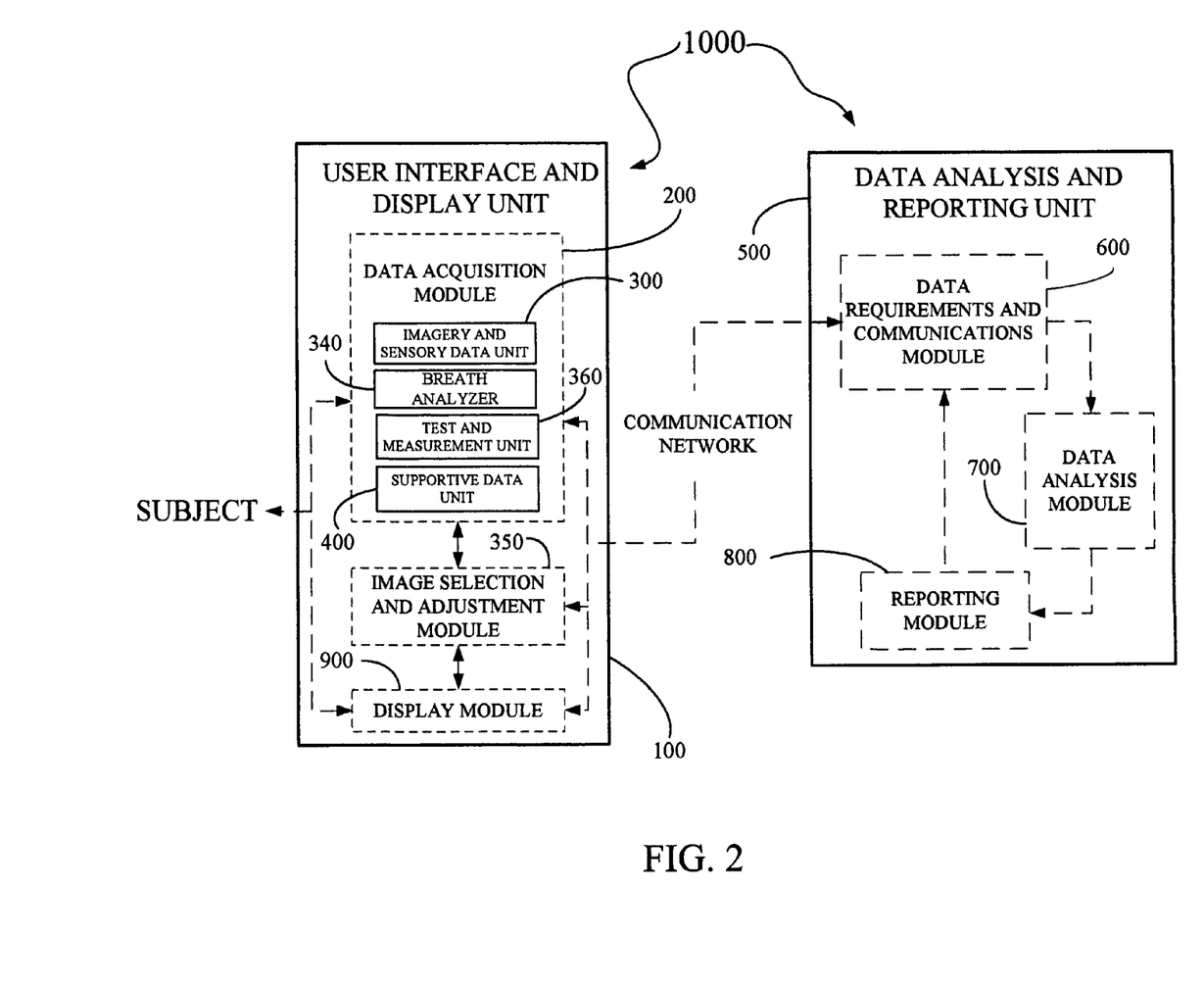
FIG. 2 is a schematic block diagram illustrating user interface and display unit 100 having a data acquisition module 200 comprising an imagery and sensory data unit 300, a breath analyzer unit 340, a test and measurement unit 360, and a supportive data unit 400, of the derma diagnostic and automated data analysis system 1000, according to an exemplary embodiment of the present invention.

Now, referring to FIG. 2, illustrated is the user interface and display unit 100 in more detail. The data acquisition module 200, of the user interface and display unit 100, works collaboratively with the remotely located data analysis and reporting unit 500 for digitally capturing a plurality of subject characteristics with an emphasis on the detection and assessment of derma or skin conditions, abnormalities and disorders. The data acquisition module 200 may comprise a imagery and sensory data unit 300, a breath analyzer 340, a test and measurement unit 360, and a supportive data unit 400.

The imagery and sensory data unit 300 digitally captures a plurality of derma characteristics that may be used to distinguish between normal and abnormal skin conditions. Multiple, usually three or more, diverse diagnostic technologies may be used to evaluate the subject's skin condition in order to detect particular characteristics of skin abnormalities, irregularities and disorders. Each of these technologies emphasizes a unique diagnostic methodology or capability and may be designed to be used conjointly with the other technologies for ensuring a thorough, comprehensive and accurate assessment will be performed.

The breath analyzer 340 may utilize a plurality of technologies to capture and analyze exhaled gases in order to identify the presence and/or concentration of certain molecules or chemical compounds that may suggest a physiological abnormality that may manifest itself as a skin condition or skin disorder.

The test and measurement unit 360 may be available in a stationary configuration or a portable configuration and may utilize a plurality of technologies to capture and digitally record certain physical and physiological characteristics as well as an array of environmental characteristics that may effect or influence the diagnostic process. The test and measurement unit 360 is also capable importing laboratory results and an array of test results acquired by external (not system 1000) devices.

The supportive data unit 400 may utilize a systematic query process to acquire personal background information, behaviors, medical histories, health background information, skin condition descriptions, genealogical predispositions, and the like. The supportive data unit 400 may also have the capability of capturing particular categories of data such as levels of pain, itchiness, discomfort, swelling, throbbing, pressure, numbness, fatigue, moodiness and the like. This category of data is systematically quantified by gauging each response against a relatively tight set of standard criteria. For example, pain is scaled in a range of 1 through 10 with 1 being a minor irritation and 10 being almost unbearable.

The image selection and adjustment module 350 maybe capable of collaboratively working with the subject, through the display module 900, and the data acquisition and reporting module 500 for ensuring the quality, accuracy and adequacy of the data being captured. For example, an operator or subject may review images to ensure the best view, of an area-of-interest, is captured or, in another case, data pertaining to a image or sensory input is correctly annotated, consistent and complete.

The display module 900 may be capable of interfacing between the subject (or an operator) and the system 1000. These interactions may be managed by the data analysis and reporting unit 500 and may include biometric identification verification sequences, security features, supportive data query presentations, query response registration, explanation presentations, test set-up instruction presentations, testing procedure presentations, image focusing, image view selection processes, captured imagery and sensory data display, test take-down instruction presentations, supportive data verification presentations, condition status report presentations, diagnosis report presentations, and the like. The display module 900 further may be capable of interfacing with the subject in order to perform monitoring, including but not limited to condition progression monitoring, treatment effectiveness monitoring, and health strategy monitoring. In such cases, the data analysis and reporting unit 500 initiates periodic monitoring sequences which may include alerts, reminders or notifications as well as specific monitoring procedures. The data analysis and reporting unit 500 may also be capable of alerting the subject of a monitoring requirement through means other than the display module 900. This may include e-mail messages, voice mail messages, mailings, and the like.

Figure 3:
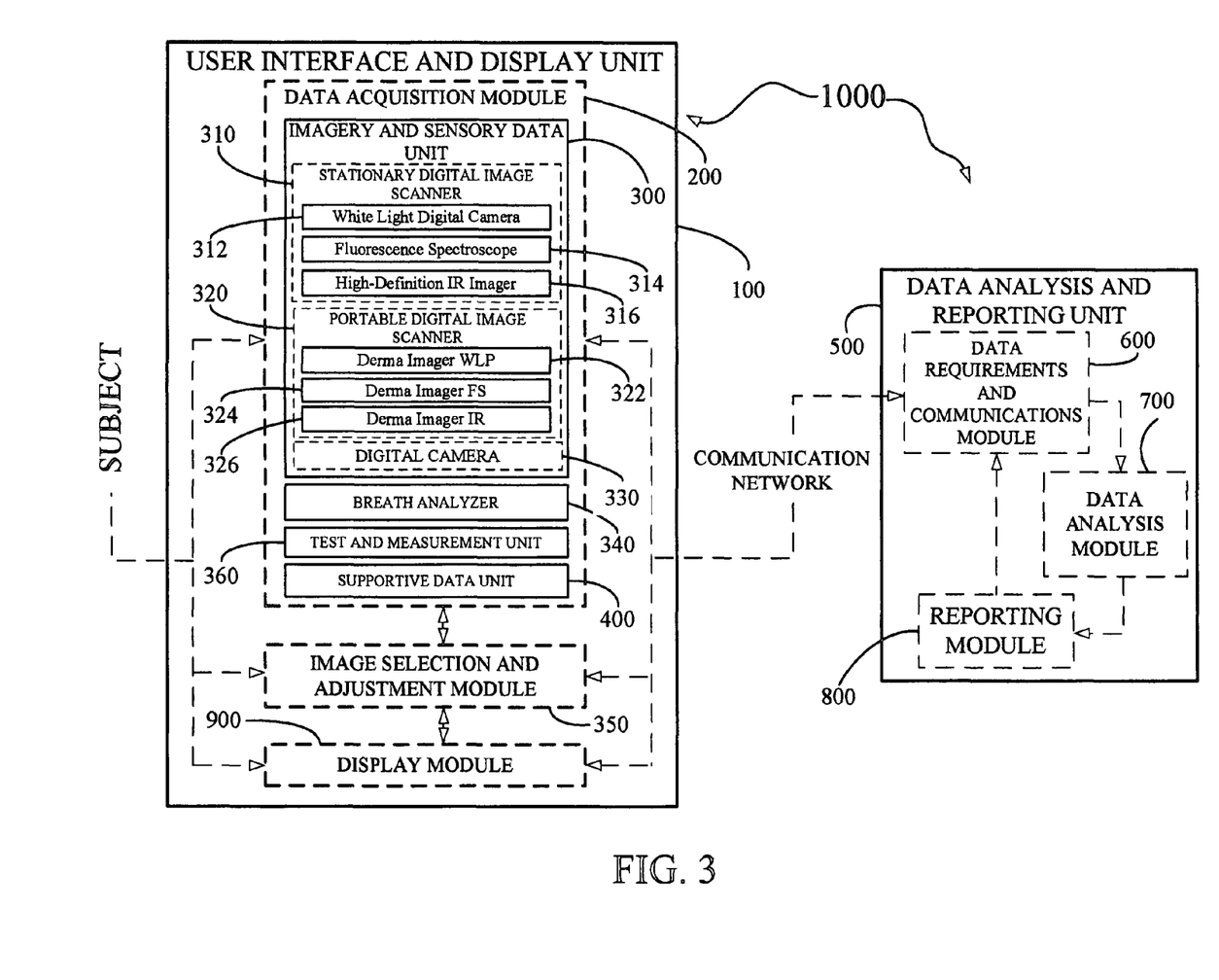
FIG. 3 is a schematic block diagram illustrating the imagery and sensory data unit 300 of the data acquisition module 200, according to an exemplary embodiment of the present invention.

Now, referring more specifically to FIG. 3, illustrated is the imagery and sensory data unit 300 of the data acquisition module 200. The imagery and sensory data unit 300 may include, but is not limited to, a stationary digital image scanner 310, a portable digital image scanner 320, and a digital camera 330. The imaging components of the imagery and sensory data unit 300 may be further communicatively coupled to the image selection and adjustment module 350 and the display module 900 in order to display and optimize the imagery data that is being acquired.

The stationary digital image scanners 310 may be divided into two configurations, namely, the horizontal digital image scanner (not shown) and the vertical digital image scanner (not shown). These devices are similar except the horizontal digital image scanner may be designed to image bodies lying in a horizontal position while the vertical digital image scanner may be designed to image bodies standing vertically or erect. The horizontal digital image scanner and the vertical digital image scanner may incorporate and use three or more uniquely different technologies that separately acquire images of particular characteristics of a skin condition or disorder. These technologies may include digital imagery white-light photographic, fluorescence spectroscopic imagery, and radiometric imagery.

The stationary digital image scanner 310 may incorporate an adjustable white-light digital camera 312 and suitable lighting, which may include a reticle projector and may be attached to the traversing head assembly of the horizontal and vertical digital image scanners, and may be remotely manipulated in multiple planes to permit optimized focusing, lighting and viewing. The white-light digital camera 312 may capture images, of areas-of-interest, either individually or by a streamed video. A scanning mode may be selected which automatically manipulates the white-light digital camera 312 to permit the scanning and imaging of an entire body or just a specific sector. The precise positioning and location of suspected abnormality may be digitally recorded in each of the photographic images by using fixed datum point triangulation using fixed landmarks and/or anatomical features. For the purpose of this invention, white-light or visible-light is electromagnetic radiation that has a wavelength in the range from about 4,000 (violet) to about 7,700 (red) angstroms and may be perceived by the normal unaided human eye. The white-light digital camera 312 may be designed to capture white-light images of high-resolution, high contrast-ratios and true color, and with high quality color saturation. These images may be precisely scaled in order to accurately depict precise dimensional characteristics that may delineate even minute differentiations in the manifestation of skin conditions and disorders. During a white-light digital camera scanning process, the captured imagery may continuously be screened in order to detect suspicious edges, shapes, colors, textures and other differentiating characteristics of a peculiar or unusual skin aberration. Once a suspected area-of-interest is detected, the white-light digital camera 312 typically focuses on the area with magnification typically ranging from 2× to 700×.

For example magnification, in the range of 160×, maybe used to detect pathogenesis associated with hair follicle mites. Magnification of greater than 700× may be available and utilized under unusual circumstances where high magnification, microscopic imaging is necessary. Images that have been photographed or videoed may be accurately scaled down to less that 1 mm at a magnification of 1×. Image quality may be reviewed and, if desired, manually optimized though the use of the image selection and adjustment module 350. In one embodiment, the magnified objects may be scaled accurate to less that 0.1 mm under higher magnification. The white-light digital camera 312 may be the lead or initial imagery technology that is applied, and may be responsible for establishing common or shared datum points that may be used to precisely locate objects within areas-of-interest.

A fluorescence spectroscope 314 may be used as a safe, noninvasive skin condition assessment or diagnostic tool that detects sizes and quantifies variances in the fluorescence landscapes and the presence of markers that may indicate a condition or tissue abnormalities. The emitter and detector, of the fluorescence spectroscope 314, may be mounted on the head assembly of the horizontal digital image scanner and/or the vertical digital image scanner and may include a reticle projector and may be positionable in the same manner as the white-light digital camera 312. Image quality may be reviewed and, if desired, manually optimized though the use of the image selection and adjustment module 350. The fluorescence spectroscope 314 may be used to scan the body's surface areas independently of other imaging devices as well as in collaboration with other imaging devices. For example, fluorescence spectroscope may scan the body for peculiarities and abnormalities without regard to areas-of-interest detected by other imaging devices and then focus the fluorescence spectra imaging on the areas-of-interest, it has detected, as well as areas-of-interest detected by the other imagers. In this way, the fluorescence spectroscope 314 may perform independent assessments as well as elaborate or expand on discoveries made by other imaging technologies.

A high-definition Infra Red (IR) imager 316 may be used to capture the sized digital radiometric images of the body's surface area and quantify minute variances in temperature by registering the radiometric values of each detector pixel. This permits the detection of hyperthermia, localized vasodialation, hypervacularization, discrete temperature variations, and other abnormalities that display unique temperature characteristics. The high-definition IR imager 316 may include a reticle projector and may be mounted on the head assembly of horizontal digital image scanner and/or on the vertical digital image scanner in the same manner as the white-light digital camera 312 and the fluorescence Spectroscope 314. Image quality may be reviewed and, if desired, manually optimized through the use of the image selection and adjustment module 350. The high-definition IR imager 316 may be used to scan the body's surface areas independently of other imaging devices and in collaboration with other imaging devices. For example, the high-definition IR imager 316 may scan the body for peculiarities and abnormalities without regard to areas-of-interest detected by other imaging devices and then focus the high-definition IR imaging on the areas-of-interest it has detected as well as areas-of-interest detected by the other imagers. In this way, the high-definition IR imager 316 may perform independent assessments as well as elaborate or expand on discovers made by other imaging technologies.

The portable digital image scanner 320, also referred to as derma imager, may consist of a set of compact, lightweight devices used to capture various characteristics of skin conditions and skin disorders. There may be one or more portable digital image scanners 320 operationally subordinate to a user interface and display unit 100 configured to facilitate access, to the system 1000, by remotely located subjects who might otherwise not have access to the stationary digital image scanners 310. The portable digital image scanner 320 may include three imager configurations in its set or suite of components. These imagers may include: a derma imager WLP (White-Light Photographic) 322; a derma imager FS (Fluorescence Spectroscopy) 324; and a derma imager IR (Thermo-Graphic IR) 326. Each of these imagers is compact, light weight and may be comfortably operated by one hand. The portable digital image scanner's 320 suite of components also incorporates a portable ruggedized computer with a high-contrast, true-color, high-resolution touch-screen display with built-in ambient temperature/air quality/humidity/elevation sensors, stylus, mouse and high-speed modem (not shown), a cable set (not shown), a battery set and charger (not shown), adapters (not shown), miscellaneous spare components (not shown), a cleaning kit (not shown), a manual (not shown), software applications and training materials (not shown) and other supporting items, all stowed in one or more ruggedized carrying cases (not shown). Data captured by the portable digital image scanners 320 may be transmitted to the portable computer which thereafter may transmits the data, via the communication network, to the data analysis and reporting unit 500. This transmission may be either direct or through the user interface and display unit 100, to which the portable digital image scanner 320 is operationally subordinate. Alternatively, the portable digital image scanner 320 may be assigned to or managed by an independent third party. In this case, the portable digital image scanner 320 may directly forward the captured data to the data analysis and reporting unit 500.

The derma imager WLP 322 may be designed to capture individual and streamed digitized photographic/video images of a similar kind and for the same purposes as the stationary digital image scanner 310 but at a slower rate and smaller scale and with fewer automated functions. The components that may be built-into the derma imager WLP 322 may include a digital camera (not shown) with high-contrast, high-resolution, true color (high color accuracy) and high quality color saturation capabilities and features. The derma imager WLP 322 incorporates: magnification selections ranging between 1× to 700×; a reticle projection device; a light meter sensor; an adjustable light source; and an appended surface texture and thickness sensor. The reticle, projected onto the skin, is used for positioning the device correctly over the area-of-interest. The video image may be transmitted to the portable computer and displayed on the touch-screen monitor. The subject may adjust the derma imager WLP 322 until the lighting, focus and view are optimized. Once the desired image is suitably displayed, the subject initiates a capture sequence. Areas-of-interest, captured by the derma imager WLP 322, may be accurately scaled down to 1 mm or smaller, at a magnification of 1× which means the dimensional size (height and width) of objects in the images may be accurately gauged. Additionally, magnified objects (greater than 2×) may be scaled accurate to less than 0.1 mm. Additionally, the derma imager WLP 322 may be equipped with self-diagnostics and self-calibration devices which permit simplified maintenance and ensure high quality performance.

The derma imager FS 324 may consist of a fluorescence spectroscope (including an ultraviolet and/or infrared emitters and detectors), a digital camera with a light meter, adjustable light source, and a reticle projector. The fluorescence spectroscope and digital camera may generate a video, of the targeted area, which may be transmitted to the portable computer and viewed on its monitor. When a suitable view has been selected, the operator may initiate a capture sequence and the images will be captured and automatically transmitted to the user interface and display unit 100 or the data analysis and reporting unit 500. Both visual images (digital photographs/video) and the fluorescent spectra data may be captured along with location identification data. Additionally, the derma imager FS 324 can be equipped with self-diagnostics and self-calibration devices which permit simplified maintenance and ensure high quality performance.

The derma imager IR 326 may consist of a thermo graphic imager or sensor, reticle projector, and a digital camera with a light meter, adjustable light source, and a reticle projector. The thermo graphic imager and the digital camera may generate a video, of the targeted area, which may be transmitted to the portable computer and viewed on its monitor. When a suitable view has been selected, the operator may initiate a capture sequence and the images will be captured and automatically transmitted to the user interface and display unit 100 or the data analysis and reporting unit 500. Both visual images (digital photographs/video) and the thermo graphic data may be captured along with location identification data. Additionally, the derma imager IR 326 can be equipped with self-diagnostics and self-calibration devices which permit simplified maintenance and ensure high quality performance.

Additionally, a standard, off-the-shelf, high quality, high-contrast, true color, high-resolution, digital camera 330, in combination with appropriate full-spectrum lighting, may be used to capture digitized photographic/video images of an object-of-interest. These images are typically not of the quality acquired by the stationary digital image scanners 310 or the portable digital image scanners 320 however, the image quality is frequently adequate to allow at least a preliminary automated analysis. This capability offers a significant advantage since digital images of derma abnormalities may be captured, by almost anyone, and electronically transmitted, over the communications network, to the data analysis and reporting unit 500 directly or through the user interface and display unit 100.

The data acquisition module 200 may incorporate a breath analyzer 340, which may be used to analyze the composition of the subject's breath in order to detect the presence and concentration of certain molecules or chemical compounds that provide markers of a physiological condition that can manifest it self in the form of skin disorders. The breath analyzer 340 is simple and easy to administer and produces near real-time and accurate assessments of the breath gasses. The subject breathes into the device through a disposable mouth-piece & cartridge assembly which may be inserted into the breath analyzer 340 housing. In one configuration of the breath analyzer 340, the breath analysis technology may utilize laser absorption spectroscopy. Near ultraviolet (UV) to near infrared (IR) wavelengths may be emitted into the gas and a spectrophotometer can be used to measure the absorption spectrum, which is recorded as a quantitative value. Absorption spectrums are unique to particular compounds and change with varying concentrations. Available technologies of breath analyzer 340, such as the gas chromatography-electrolyzer powered flame ionization detector (EFID) may also be used The output of the breath analyzer 340 may be transmitted to the data analysis and reporting unit 500 directly or through the user interface and display unit 100.

The data acquisition module 200 may incorporate a test and measurement unit 360 as a stationary and portable configuration. The test and measurement unit 360 may be used to capture quantitative physical characteristics and physiological characteristics of the subject, as well as test environment characteristics (including calendar day, time-of-day, and location). Additionally the test and measurement unit 360 is capable of importing outside laboratory results and test results.

The physical characteristics or features, captured by the test and measurement unit 360, include height, weight, body dimensions, body fat ratios, skin tone/shade, fingernail characteristics, eye color, hair color, and the like. The physical features may be captured for the purposes of developing a comprehensive physical description of the subject, including both their peculiar or unusual characteristics and their common or normal characteristics.

The physiological characteristics, captured by the test and measurement unit 360, include vital signs, bone density, muscular/skeletal strength and flexibility, arterial blood oxygen saturation, endurance, skin thickness, skin texture, skin translucence, skin elasticity, skin moisture content, skin sensitivity, vision, eye clarity, hearing, hair loss and hair condition, fingernail characteristics, hormone levels, and the like. The physiological characteristics may be captured for the purposes of developing a comprehensive physiological description of the subject, including both their common or normal characteristics as well as their abnormal or peculiar characteristics.

The test environment characteristics, captured by the test and measurement unit 360, include ambient temperature, air quality, humidity, elevation, air pollutants, geographical location, and calendar day and time of day. The test environment characteristics may be captured for the purposes of defining those influencing environmental factors that may affect test results.

The test and measurement unit's capability to import laboratory test results and test results captured by external test equipment is provided for the purposes of including potentially important diagnostic data elements, developed outside of the system 1000. This enables the capability for ensuring the broadest practicable selection of test and measurement data is captured and made available to the data analysis and reporting unit 500 for analysis.

The data acquisition module 200 may be responsible for the acquisition of prescribed data elements as quantitative values. These data elements are derived from continuously evolving sets of tests, measurements and background queries and may comprise essential prerequisite source data for the high-speed automated analysis preformed by the data analysis and reporting unit 500. These data elements may include imagery data (or spectral data), sensory data, physical/physiological and environmental test and measurement data, and supportive data. Imagery data may be collected by the white light digital camera 312 (including but not limited to the dermatoscope and videomicroscope), fluorescence spectroscope 314, high-definition IR imager 316, derma imager WLP 322, derma imager PS 324, and the derma imager IR 326, and, additionally by the independently operated digital camera 330. These devices may be designed to detect and quantitatively register particular visual, florescent and/or thermal characteristics of skin conditions and skin disorders. For capturing the appearance, size, shape, color, edge characteristics, spectral characteristics, and density characteristics of skin conditions and disorders, other additional technological applications such as, ultrasonography and optical coherence tomography may also be used. Sensory data may be collected by the breath analyzer 340 which may include, but is not limited to, laser absorption spectroscopy and gas chromatography technologies. The breath analyzer 340 may be designed to detect and quantitatively register chemical compounds or markers, in the subject's breath, that correlate to certain known conditions, diseases, toxicity/poisoning, inflammation, or other types of disorders or abnormalities. The breath analyzers may also be used to detect evidence or indications of dietary/nutritional deficiencies, hormonal imbalances, drug and alcohol abuse, drug interactions/reactions, and the like. The test and measurement unit 360 may be designed to digitally acquire at least two categories of data which includes physical/physiological characteristics and test environment characteristics. The physical and physiological characteristics include information such as height, weight, body fat ratio, body dimensions, vital signs, vision performance, hearing performance, coordination, strength, flexibility, arterial blood oxygen saturation, blood type, skin texture, skin thickness, skin elasticity and the like. The test environment data includes ambient temperature, air quality, humidity, air quality, and elevation.

Additionally, data originating form other sources (i.e. laboratory reports, medical histories, skin tests, blood tests, biopsies, and the like) may also be imported into the user interface and display unit 100, through direct entry or the use of a communication network such as high-speed internet connection or the like. Once the key data prerequisites have been verified, the user interface and display unit 100 transmits the data, through the communication network, to the data analysis and reporting unit 500 for processing and subsequent analysis.

The digitized imagery, measurement, and sensory data, that have been captured by the imagery and sensory data unit 300, may be submitted to the image selection and adjustment module 350 where the data is processed for presentation by the display module 900. Once displayed, the subject or the operator may make image selections, modify or add references or data elements, verify dimensional data, verify area-of-interest location designators, modify or add narrative, adjust image quality, and perform a number of other material enhancement and equipment operational verification and maintenance tasks through the use of the user-interface devices (i.e. touch-screen display, stylus, key board, mouse, etc.) incorporated into the display module 900. Commands, entered through the display module 900 user-interface devices, may be routed to the image selection and adjustment module 350, which interprets the inputs, acts on the commands, and/or disseminates instructions to other modules or units including the imagery and sensory data unit 300, breath analyzer 340, test and measurement unit 360, and the supportive data unit 400.

Figure 4:
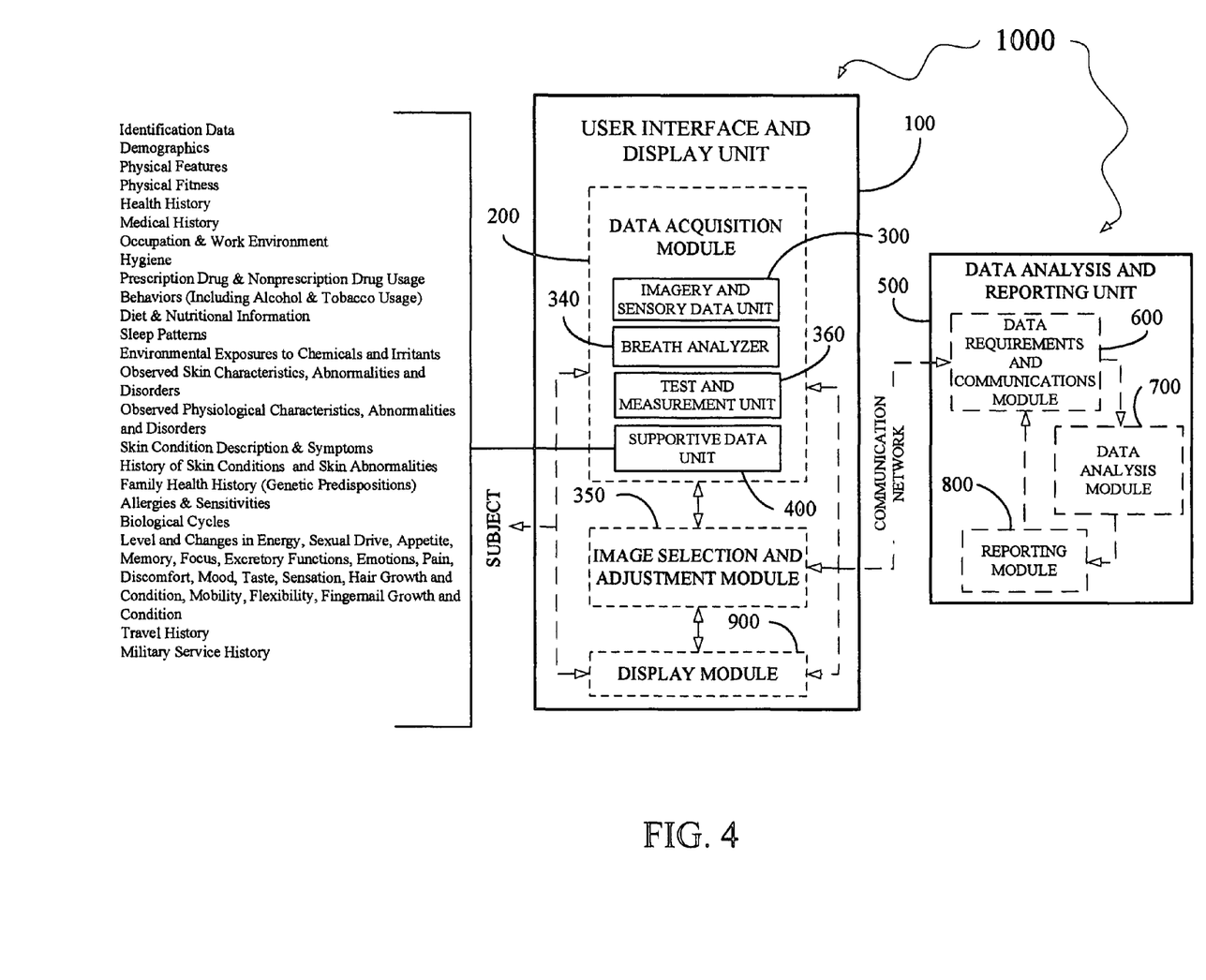
FIG. 4 is a schematic block diagram illustrating the supportive data unit 400 of the data acquisition module 200, according to an exemplary embodiment of the present invention.

Referring to FIG. 4, illustrated is the supportive data unit 400 of the data acquisition module 200. The various data acquisition features of the supportive data unit 400 may be automatically initiated, by the data analysis and reporting unit 500, whenever: certain background data and condition descriptive data is required for new clients; updated data is required to support a condition monitoring activities; updated information is required to support treatment and health strategy effectiveness monitoring activities; database updates are needed due to data inconsistencies or outdated material; imagery and/or sensory data inputs reveals insufficient, inconclusive, inconsistent or missing supportive data; analysis reveals a need for additional supportive data; and the like. The network of user interface and display units 100, including the supportive data unit 400, function as extensions of the centrally located data analysis and reporting units 500. The supportive data unit 400 may be designed to digitally acquire a broad array of personal identification data and background health information such as demographics, personal health history, family health history (i.e. health history of blood relatives), medical history, diet/nutrition, environmental exposures, occupational exposures to noxious and toxic substances, and behaviors (i.e. alcohol, tobacco and drug usage). Additionally the supportive data unit 400 may capture specific symptomatic data such as: condition history, physical symptoms (i.e. swelling, itchiness, pain, discharges, burning, numbness, dryness, scaling, heat sensitivity, cold sensitivity, etc.); symptom severity; symptom progression; and the like. The supportive data unit 400 offers a host of data acquisition features and is designed to present a series of queries that are personalized to the unique characteristics of the subject. Subject responses are assessed and logical follow-up queries are generated and pursued in a series of query tiers. The query process may focus on both targeted objective (i.e. establish personal identity characteristics, establish health histories, establish medical histories, collect condition monitoring data, collect treatment effectiveness monitoring data, establish predispositions, identify drug usage, identify behaviors, and so on) or key response elements that suggests more information (i.e. follow-up queries) may be required to adequately document the subject's condition or situation.

The supportive data unit 400, in collaboration with the data analysis and reporting unit 500, may be designed to acquire data, that includes but is not limited to: personal identification information such as name, address, phone number, e-mail address, and the like; demographics data such as age, gender, race, ethnicity, educational level, occupation, sexual preference, marital status, children, religion, recreational activities, and the like; physical features such as hair growth, hair color, eye color, skin tone, fingernail condition, posture, and the like; physical fitness including activity level, relative strength, energy level, coordination, disabilities, deformities, and the like; health history, medical history data; occupation environment including exposure to radiation, poisons, and other noxious and toxic substances and irritants; hygiene; prescription drug and nonprescription drug usage; behavioral data including alcohol and tobacco usage; diet and nutritional information; sleep patterns; non-occupational environment including exposure to radiation, poisons and other noxious substances and irritants; observed skin characteristics, abnormalities, and disorders; observed physiological characteristics, abnormalities and disorders; and the like.

Figure 5:
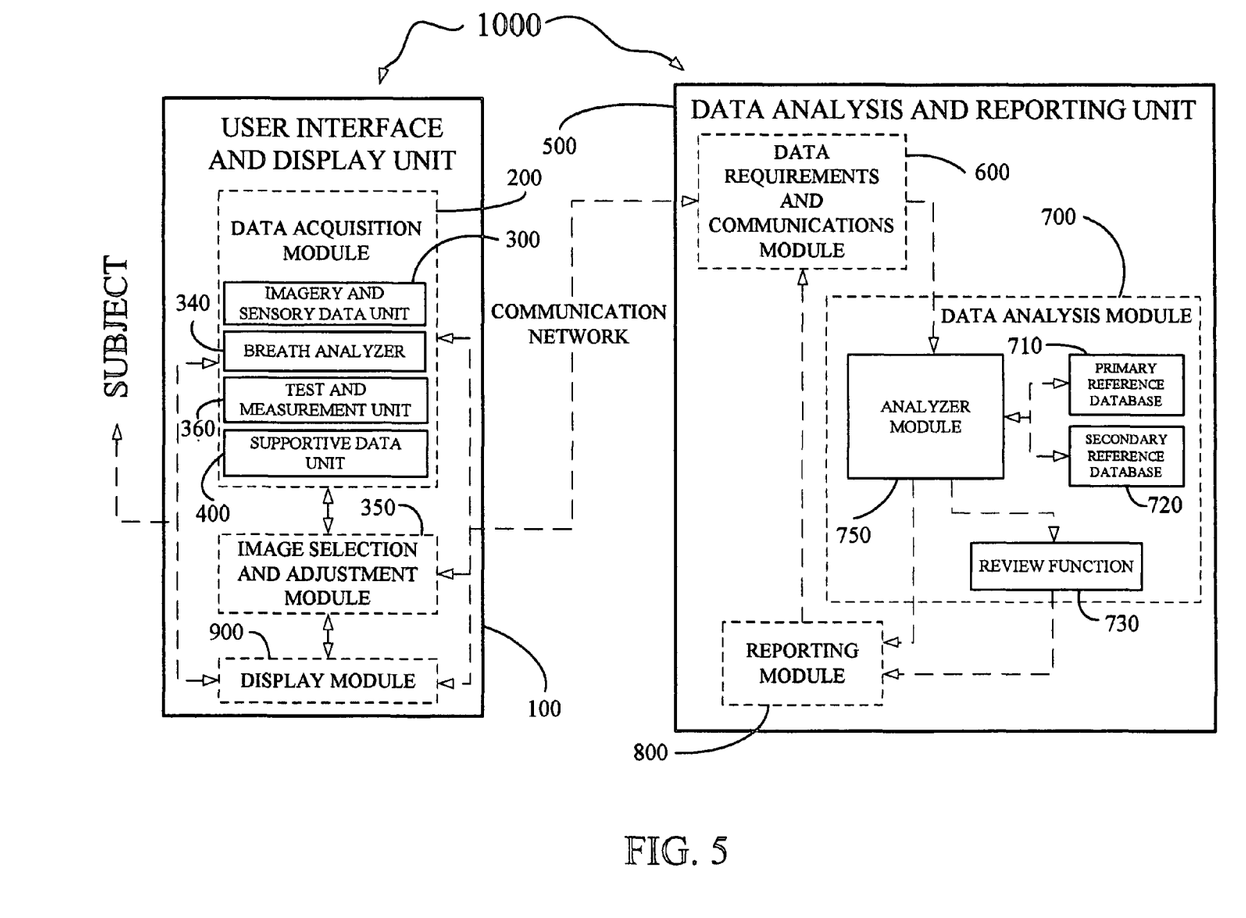
FIG. 5 is a schematic block diagram illustrating data analysis and reporting unit 500 having a data requirements and communications module 600, a data analysis module 700 and a reporting module 800, according to an exemplary embodiment of the present invention.

Referring to FIG. 5, illustrated is the data analysis and reporting unit 500. The data analysis and reporting unit 500 may be remotely located and connected to the user interface and display unit 100 over the communication network such as internet. The data analysis and reporting module 500 may consist of a data requirements and communications module 600, a data analysis module 700, and a reporting module 800. The data requirements and communications module 600 may be capable of interacting with the network of user interface and display units 100 in order to facilitate user interactions and the exchange of information, acquire prescribed imagery data, sensory data, test and measurement data, and supportive data, managing the implementation of condition monitoring programs, and transmit health status reports. The data requirements and communications module 600 may be communicatively linked to the user interface and display units 100 or more specifically the data acquisition module 200, image selection and adjustment module 350, and the display module 900 through the communication network. The interactions between these units and the data requirements and communications module 600 is transparent to the subject whereas the user interface and display units 100 provide the interface with the subject, the data analysis and reporting unit 500 provides centralized data processing and analysis capabilities as well as a host of integrated database reference libraries.

The data requirements and communications module 600 may be capable of processing and preparing sensory data, test and measurement data, and supportive data, received from the user interface and display units 100, for analysis by the data analysis module 700 and the establishment of population groups that share similar characteristics. The data preparation may include: screening the data for completeness; categorizing the data by demographic characteristics such as age, gender, race, ethnicity, sexual preference, marital status, children, geographical location, recreational activities and occupation; categorizing the data by physical features such as height, weight, body fat ratio, body dimensions, skin tone, hair color and growth, and eye color; categorizing the data by physiological characteristics such as heart rate, respiratory rate, blood type, blood pressure, blood chemistry composition, exhaled gas chemistry composition, and temperature; categorize the data by preexisting medical conditions, prescription drug usage, medical treatments, and disabilities; categorize the data by shared behaviors; categorize the data by diet and nutritional characteristics; categorize the data by environmental exposure to specific toxic or noxious substances; categorize the data by infestation by specific parasites; categorize the data by fungal infections; categorize the data by dermal injuries; and the like. This preparation is used to pre-select comparative population groups, expedite the analysis process and enhance the effectiveness and speed of the analysis.

Additionally, the data requirements and communications module 600 may be responsible for data security and operational availability monitoring and system diagnostics and maintenance.

The data analysis module 700 may be considered to contain the core intellect of the system 1000. The data analysis module 700 is configured to: collect a diverse range of quantitative data elements which include demographic, historical, physical, physiological, behavioral and psychological characteristics and a plurality of test results which are categorically grouped and organized by the data requirements and communications module 600; systematically analyze the data elements; develop a primary and one or more secondary diagnoses (meaning treatments for the primary diagnosis may normally not be incompatible with treatments of the secondary diagnosis, particularly when the analysis of the available data indicates relatively little difference in which diagnosis is most probably correct); identify effective treatments, for the subject's skin condition, that are compatible with the subject's unique characteristics, behaviors and preferences; establish condition monitoring parameters; establish treatment effectiveness monitoring parameters; and develop health strategies (i.e. avoidance and mitigation strategies and health enhancement strategies).

The data analysis module 700 may incorporate multiple analytical methodologies that are based on deductive and inductive reasoning processes. The core analytical methodologies may include: comparative analysis; pattern and trend analysis; correlation analysis; risk analysis; and health strategy development.

Comparative analysis may be comprised of multiple elements. This includes the comparison of individual and combined imagery, sensory, test and measurement, and supportive data elements against each other in order to identify peculiarities, establish relationships and confirm consistency or continuity. Comparative analysis also includes the comparisons of individual and combined data elements against equivalent data elements associated with population groups sharing similar skin conditions, abnormalities, disorders, demographics, physical/physiological/psychological/behavioral characteristics, diets, and historical characteristics (i.e. medical history, robustness, health condition histories, rates of recovery, prescription drug usage characteristics, etc.), and the like. It is unlikely that a single population group would share all or even most of the same characteristics as the subject. Therefore, comparative populations groups are tailored to incorporate certain critical or core shared characteristics (i.e. age, gender, and race) first and then systematically expanded to share other characteristics in whatever combinations that are logical. In one form of comparative analysis, the comparison process may include the comparison of test results captured by diverse technologies. For example, imagery data, captured by a fluorescence spectroscopic device, may be compared to imagery data captured by a high-definition IR imaging device. In this case, the comparisons are performed in order to identify similarities and dissimilarities, in the resulting test data, that would tend to support a diagnosis or indicate whether additional analysis is required. The information that is derived from data element comparison and comparisons to similar population groups may reveal subject peculiarities and/or abnormalities that may not otherwise be evident. In comparative analysis, the related individual data elements, collective data elements and test results may continuously be updated and subjected to additional comparison. If new data causes an irregularity in the comparisons, the incongruency is gauged for severity and the impact on the current diagnosis and treatment is assessed.

Pattern and trend analysis may utilize an assessment of individual or various combinations of imagery data elements, sensory data elements, test and measurement data elements, and supportive data elements in order to identify the presence of similarities and regularities in results and/or behaviors, as well as natural classifications or clusters of data. Additionally, the patterns are assessed individually, in various combinations and cumulatively. New data element inputs may cause a reassessment of current patterns. When a pattern deviation is detected, it is gauged for severity and the impact on the current diagnosis is assessed. Patterns are continuously monitored in order to identify directional tendencies to change-over-time (also known as trends) and to identify the stability of the subject and the severity and direction of change. A file may be established that represents the subject's "normal" condition (not necessarily indicating the subject's condition is normal) across a broad range of characteristics. This file is continuously updated and the patterns and trends analysis program is sensitized to detect deviations from the subject's norm Correlation analysis may be performed in order to identify relationships between similar and diverse data elements in order to better establish the nature, cause, severity, and most effective treatment of a skin condition. Data correlations are more tightly focused by sensitizing the correlations to the subject's age, gender, race, ethnicity, geographical location, and other influential factors. The correlation analysis process may be comprised of multiple segments which include: systematically cross-correlating the subject's individual test results and data elements (including imagery data, sensory data, test and measurement data, and supportive data) against each other, systematically cross-correlating various combinations of data elements and test results against other individual and combinations of data elements and test results; systematically cross-correlating the subject's data elements and test results against authoritative standards, research, studies, reports, and other credible reference materials.

Risk analysis may be comprised of systematic procedures that identify and analyze the subject's health threats and health vulnerabilities. These may include: risks related to the skin condition's symptomology; risks pertaining to influencing factors (i.e. age, medical conditions, health conditions, occupation, diet, hygiene practices, environmental exposure, and the like); risks related to one diagnosis versus another diagnosis; risks related to the treatment options; risks associated with condition degradation if treatment is ineffective; risks associated with alternative diagnoses; risks associated with alternative treatments; risk of a contagion, risk to fertility, risks during nursing; risks during pregnancy; and the like. The subject's probable exposure to the risk(s) is ascertained and calculated. The risk analysis program may then offer a plan or strategy for risk avoidance, risk mitigation, and risk monitoring.

Health strategy analysis may be comprised of a systematic assessment of the subject's physical characteristics, physiological characteristics, psychological characteristics, health condition, medical conditions, behaviors, family health history (genetic predispositions), diet and eating habits, sleeping habits, nutrition, activity level and fitness, prescription drug and non-prescription drug usage, occupation, environmental exposures, living environment, work environment, chemical exposures, travel, recreational activities, hygiene, lifestyle, and the like. Additionally, the subject's age, gender, race, ethnicity, geographical location, marital status, religion, emotional condition, educational level, sexual interest and activity level, and the like may be taken into consideration. The health strategy analysis is performed in order to identify those exposures, behaviors and other elements, of a subject's condition or lifestyle that may be creating an unhealthy situation that may cause or exasperate the subject's susceptibility to illness, disease, injury, contamination, infections, infestation, premature aging, and other causes of distress, and anguish. Once these elements are identified, the health strategy analysis process develops a detailed personalize plan or strategy that systematically incorporates a sequence of unique features that are designed to target certain unhealthy hygiene issues, exposures, behaviors, nutritional deficiencies and the like. Additionally, they may be designed to sensitize the subject to the need to avoid, or protect themselves against, unhealthy substances, irritants, parasites, fungus, and microbes that they may be exposed to in their particular home or work environments. The health strategy analysis also offers listings of safe and effective hygiene and skin care products that may be designed to be compatible with the subject's own unique characteristics. The purpose of the health strategy analysis may be to enhance or augment the subject's overall health and wellbeing through healthy behaviors, nutrition, practices, and products. To ensure effective implementation, the health strategy analysis process establishes a realistic schedule, achievable milestone objectives, and a set of monitoring parameters.

Analyzer module 750 of the data analysis module 700 maybe capable of performing technical analysis of data categories including imagery data, sensory data, test and measurement data, and supportive data. Imagery data may include digital photographic imagery data, radiographic imagery, and fluorescent spectra imagery. Sensory data may include breath-gas analysis data elements. Test and measurement data may include a host of physical physiological, and environmental test and measurement data elements. Supportive data may include a host of descriptive data elements. Each of these categories of data may be captured by diverse and sophisticated technologies. The analyzer module 750 can provide technical analysis processes that incorporate methodologies such as scientific/technical assessments, comparative analysis, patterns and trends analysis, correlation analysis, risk analysis and the like.

The analyzer module 750 may incorporate a digital photographic imagery data analysis function that may filter (screens), process, segment and categorize the imagery inputs from devices such as the white-light digital camera 310, derma imager WLP 322, and the digital camera 330, in order to establish usable material, tables and files of quantitative data that may be structured in a manner that would facilitate, among other things, technical analysis, comparative analysis, pattern and trend analysis, data correlation analysis and risk analysis. The digital photographic image analysis may be used to formulate and assess specific image characteristics that may include appearance, size, shape, edge characteristics, color, and the like. The appearance characteristic may address the high-contrast, high-resolution and accurately scaled images of distinctive phenomena, objects and object clusters within an area-of-interest. The size characteristic may address the precise quantitative representations of the size of distinctive phenomena, objects and object clusters within an area-of-interest. The shape characteristic may address the precise quantitative representations of the shape of distinctive phenomena, objects in the area-of-interest. The edge characteristic may address the precise quantitative representations of the edge characteristics of distinctive phenomena, objects within the area-of-interest. And color characteristic may address the precise quantitative representations of color (including color accuracy and color saturation) of the phenomena and/or objects within the area-of-interest.

The analyzer module 750 may incorporate a radiographic image data analysis function that may filter (screens), process, segment and categorize the radiographic imagery inputs from devices such as the high-definition IR imager 316 and the derma imager IR 326 in order to establish usable tables and files of quantitative data that may be structured in a manner that would facilitate, among other things, technical analysis, comparative analysis, pattern and trend analysis, data correlation analysis and risk analysis. The radiographic image analysis function may be used to formulate and assess specific radiographic images that may be used to establish quantitative values depicting the precise temperatures and temperature differentiations of the phenomena and/or object, in the area-of-interest, and the surrounding tissues.

The analyzer module 750 may incorporate a fluorescent spectra data analysis function that may filter (screen), process, segment and categorize the fluorescent spectrographic inputs from devices such as the fluorescence spectroscope 314 and the derma imager FS 324 in order to establish usable tables and files of quantitative data that may be structured in a manner that would facilitate, among other things, comparative analysis, pattern and trend analysis, data correlation analysis and risk analysis. The fluorescent spectra analysis function may be used to formulate and assess specific fluorescent spectrographic images that may be used to establish quantitative values depicting the precise fluorescent spectrographic emission characteristics of the phenomena and/or object in the area-of-interest.

The analyzer module 750 may incorporate a breath-gas analysis function that may filter (screen), process, segment, and categorize data inputs that include but are not limited to, laser absorption spectrographic data and gas chromatography data, captured by devices such as the breath analyzer 340. The breath analysis process establishes usable tables and files of quantitative data that may be structured in a manner that would facilitate, among other things, comparative analysis, pattern and trend analysis, data correlation analysis and risk analysis. The breath analysis function may be used to identify and assess specific chemical compounds, molecules, and markers that may be used to establish precise quantitative depictions of the substances present in the subject's breath.

The analyzer module 750 may further incorporate a test and measurement data analysis function that may filter (screen), process, segment and categorize a host of test and measurement inputs, from the test and measurement unit 360, in order to establish usable tables and files of quantitative data that may be structured in a manner that would facilitate, among other things, comparative analysis, pattern and trend analysis, data correlation analysis and risk analysis. The test and measurement analysis function may be used to formulate and assess specific physical and environmental characteristics that may be used to develop precise quantitative depictions of the subject's physical characteristics, vital signs, strength, vision, hearing, sensitivity to pain/touch/hot/cold, physical features of the skin condition (i.e. surface texture and moisture content, density, thickness, etc.), test environment (ambient temperature, humidity, elevation, etc.), and the like.

The analyzer module 750 may also incorporate a supportive data analysis function that may filter (screen), process, segment, and categorize supportive data inputs from the supportive data unit 400. The supportive data analysis process establishes usable tables and files of quantitative data that may be structured in a manner that would facilitate, among other things, comparative analysis, pattern and trend analysis, data correlation analysis and risk analysis. The supportive data analysis function may be used to identify and assess specific personal, physical, physiological, psychological, and behavioral characteristics as well as family health histories, military service, occupation exposures, health histories, medical histories, prescription drug usage, travel, diet and eating habits, home environment, work environment, personal hygiene, recreational activities, exposure to sunlight, exposure to chemicals, perceived sensitivity to pain and touch, and the like. The subjective data analysis may be used to establish precise quantitative depictions of the subject's background and history.

The analyzer module 750 utilizes at least two reference databases which include primary reference database 710 and secondary reference database 720. These reference databases represent a comprehensive collection of specially formulated materials that address the quantitative characteristics of skin conditions, irregularities, abnormalities and disorders, organized with sensitivity to age, gender, race, ethnicity, geographical area, educational level, occupation and the like. Also, addressed are treatments (including success rates, complications, adverse reactions, effectiveness monitoring parameters, side effects, etc.), skin disorder avoidance and mitigation strategies, diets/nutrition, cosmetics—effectiveness and safety, health optimization strategies, and other materials that would support the diagnosis, treatment, monitoring (including condition monitoring and treatment effectiveness monitoring), avoidance and mitigation strategies, and health enhancement strategies. The authoritative standards and reference materials are comprised of a broad range of current scientific data, medical data, health studies, nutritional/dietary data, nuclear and biochemical data, demographic data, census data, gender specific research, geriatric research, cosmetic data, parasital data, fungal data, physiological data, genealogical data, and other like data and a host of authoritative standards that are in various ways associated with known skin disorders. A key element of this analytical process is the cross-correlation of the multiple data elements utilizing both deductive and inductive reasoning.

The primary reference database 710 may include a vast array of quantitative materials derived from demographic data, census data, scientific studies, medical journals, nutritional and diet data, medical encyclopedias, pharmaceutical data, health research, vitamin and mineral supplement directories, hazardous substance identification and exposure effects data, environmental health data, occupational health data, household chemical research (i.e. detergents, cleaners, soaps, shampoos, bubble baths, polishes, waxes, polishes, air fresheners, etc.), research data, personal hygiene data, cosmetics and skin care research data, occupational exposure to hazardous materials, and the like. These materials may be specifically created, altered, tailored, and/or customized to facilitate rapid search features and data cross-correlation functions of the system 1000. The database architecture, structure, and organization may be optimized to ensure fill compatibility with the analyzer module 750.

The secondary reference database 720 may consist of quantitative materials derived from sources that may be considered to represent lesser quality. This data will have been carefully compiled, modified, and enhanced where necessary. However, this data may lack some of the attributes and graphical imagery found in the primary reference database 710. The secondary reference database 720 may be selected for use because it depicts certain key quantitative identifiers of skin conditions that may not yet have been incorporated into the primary reference database 710. This information may be new or it may not incorporate all of the data elements necessary for inclusion in the primary reference database. In many cases, the secondary reference database 720 addresses the most recent information, research or studies, or it may address fragmented, incomplete or only partially substantiated information that may relate to more unusual or exotic skin conditions, abnormalities and disorders.

The analyzer module 750 may incorporate a diagnostic reconciliation step, where two or more possible skin condition diagnoses may be subjected to further analysis that culminates in the identification of one, most probable diagnosis. The alternative or second, third, fourth, and fifth most probable diagnoses may also be retained and referenced during the reconciliation step to ensure the primary diagnosis, and its prescribed treatment(s), are reasonably compatible with the second, third, fourth, and fifth most likely diagnosis. Meaning that if the primary diagnosis is only marginally more probable than a secondary diagnosis, the prescribed treatment may not cause harm or unnecessary risk to the subject, if it turns out the secondary diagnosis was correct. As the confidence in the primary diagnosis increases, the tolerance of risk increases slightly. The treatment effectiveness monitoring activity may be also sensitized to the alternative diagnoses and treatments so that certain peculiarities or responses to a treatment may be correlated to the corresponding response characteristics of one or more of the alternative diagnoses. If there is evidence that the treatment is ineffective against the primary diagnosis and/or if the subject's response to the treatment correspond to one or more unique response characteristic associated with one of the alternative diagnoses, the initial diagnosis is automatically reassessed and, when appropriate, the treatment is modified and a re-diagnosis is initiated.

The analyzer module 750 may generate an automated diagnosis (also known as the computer generated diagnosis), which is derived from the reconciliation step. The automated diagnosis then may be sent to either the review function 730 or the reporting module 800.

When laws, regulations, policy, rules, procedures and practices require an appropriately trained and licensed physician review and approve a diagnosis, the automated diagnosis maybe sent to the review function 730. The review function 730 may be comprised of one or more qualified and licensed physicians that systematically review the automated diagnosis to verify its accuracy and completeness. This means the basis of the automated diagnosis, including the application of analytical methodologies, and the detailed analytical processes (i.e. imagery analysis, sensory analysis, test and measurement analysis, supportive data analysis, and the like) is examined. Also each premise, upon which the diagnosis was made, is reviewed. Upon a satisfactory review of the supporting materials, the diagnosis is routed to the reporting module 800 for transmission (over the communications network) to the appropriate user interface and display unit 100 for presentation to the subject The automated diagnosis may be directly routed to the reporting module 800 when the receiving party is a duly licensed and qualified medical practitioner who is legally authorized to receive, review and concur with the diagnosis, or when laws, regulations, policies, rules, procedures, standards and practices permit the direct submission, of computer generated diagnoses, to the subject. The analyzer module 750 may incorporate numerous fail-safes and cross checks that ensure compliance to a comprehensive and thorough review of each phase or step of the process. In this way, the automated diagnosis is expected to be at least as accurate as one made by a typical physician.

The reporting module 800 may be responsible for acquiring the diagnosis, from the analyzer module 750 or from the review function 730, and generating a diagnostic health report. The diagnostic health report may have two formats, namely plain language report format and medical report format. The plain language report format can be designed to be read by a person with no medical training and limited education. The plain language report format includes information, such as, but not limited to condition description, severity, progression, probable cause and proposed treatments. The medical report format may be designed to be read by the subject's physician. It includes more technical description of the condition, such as medical description, progression, basis of diagnosis, relevant history, reference data, and the like.

Once the health report is generated, the health report may be automatically transmitted to the user interface and display unit 100 over the communication network, and may be displayed to the subject using the display module 900. Additionally, the subject may be given an opportunity to ask questions and request various summaries of the analysis process.

The analyzer module 750 may construct and implement a sequence of monitoring processes and health strategies which may be designed to ensure oversight of the subject's condition and oversight of the treatment administration as well as offer techniques and methodologies to avoid, mitigate, or prevent skin irregularities and disorders.

The monitoring processes may include condition-monitoring and treatment/strategy effectiveness-monitoring. The condition monitoring may address the monitoring of a health condition or, more specifically, the monitoring of the progression of skin conditions and health conditions that manifest themselves as skin disorders. This monitoring may be also sensitized to identify influencing factors such as time of day, date/season, biological cycles, and changes in diet, travel, recreational activities, schedules, work environment peculiarities, stress, and the like. The treatment/strategy effectiveness-monitoring may address the effectiveness of a treatment and/or health strategy on a specific condition, and its effect on the subjects overall health and performance. Additionally, treatment effectiveness-monitoring may be designed to: monitor and gauge the effects of a treatment on a diagnosed condition; and to monitor and gauge the subject's reactions to a treatment, and how the reaction correlates to anticipated reactions, plus how the reactions correlate to reactions associated with one or more of the alternative diagnoses.

The avoidance and mitigation strategies may include: enhanced sensitivity to proper hygiene, behaviors, diet/nutrition; recognition of environmental irritants, parasites, infectious diseases, hazardous microorganisms, hazardous chemicals, poisons, harmful cosmetics, funguses, and environmental exposure (i.e. sun, wind, rain, dampness, dryness, etc.); and personalized strategies for cause avoidance and/or condition mitigation. Avoidance strategies may address techniques and methods of identifying and avoiding certain situations, exposures, environments, substances, conditions, and behaviors, that are know to cause or exasperate, or may cause or exasperate adverse skin reactions in the subject. Mitigation strategies may address certain individualized techniques, methods, and practices that are known to alleviate, or may alleviate symptoms of a condition and/or disorder.

The health optimiztion strategies may include a series of highly personalized techniques, methods, behaviors and practices that may enhance the wellness and robustness (i.e., the ability to usually resist becoming ill or injured, the ability to experience less severe symptoms and/or complications when becoming ill or injured, and the ability to recover quickly, with minimal external intervention, when becoming ill or injured) of the subject while considering their age, gender, race, ethnicity, geographical location, physical characteristics, occupation, fitness, health, medical conditions, recreational activities, lifestyle, preferences, and the like. Health optimization strategies may include diet/nutritional programs, vitamin and mineral supplement regimens, exercise programs, behavior modification programs, stress management programs, hygiene, selection and application of cosmetics and perfumes, selection and application of skin care products, selection and usage of soaps/detergents/shampoos, and the like. Health optimization strategies may be designed to optimize the subject's health and, by doing so, minimize susceptibility to illness and disease as well as minimizing the adverse effects of aging.

Hereafter, the reporting module 800 may submit reports to the data analysis module 700 and where the data analysis module 700 archives the acquired subject data (i.e. imagery data, sensory data, test and measurement data, and supportive data), diagnoses, prescribed treatments, monitoring data, and health strategies, along with the key premises and authoritative standards that form the bases of the diagnosis. The cumulative data (the data compiled from the full population of subjects as well as various combinations) is assessed, by the data analysis module 700, in order to establish population patterns and trends, and to identify peculiarities and abnormalities. The cumulative assessment is used to evaluate the accuracy of the diagnoses and the effectiveness of the treatments and health strategies. Certain important diagnostic and treatment factors can be derived from this assessment. These factors include but are not limited to: demographic characteristics that can most consistently and effectively influence the establishment of a highly-probable diagnosis and most effective treatment; physical, physiological, psychological, and behavioral characteristics that can most consistently and effectively influence the establishment of a diagnosis and the effectiveness of a treatment; health history, medical history, and family health history (i.e. genealogical relationships) characteristics that can most consistently and effectively influence the establishment of a diagnosis and the effectiveness of a treatment; what skin/health condition symptoms can most consistently and effectively be used to establish a highly-probable diagnosis and effective treatment; which treatments are most effective in treating a particular symptom or combination of symptoms; what are the best and quickest indicators that a treatment is effective; what are the best and quickest indicators that a treatment is not effective; what are the best and quickest indications that the administration of a treatment is excessive or inadequate; what are the best and quickest indications that a diagnosis is incorrect; what are the best and quickest indicators that there are two or more conditions simultaneously present; what are the most probable causes of a specific condition; what conditions are most likely to appear or cluster in a specific geographical area; what skin conditions are most likely to be associated with a particular occupation; which of two or more treatments is most effective; and combinations of two or more of the above. Additionally, the assessment of the archive can identify outbreaks or unusual phenomena that may indicate early evidence of some form of contamination or epidemic. The above factors are automatically referenced and may result in readdressing a diagnosis or treatment. Copies of the archived diagnoses, treatments, monitoring results, medical history, health history, family health history, and physical/physiological/psychological and behavioral characteristics may be rapidly retrieved, by the subject or their representative (including emergency medical practitioners), at a future date.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is understood that various omissions, substitutions of equivalents are contemplated as circumstance may suggest or render expedient, but is intended to cover the application or implementation without departing from the spirit or scope of the claims of the present invention.

What is claimed is:

1. A derma diagnostic and automated data analysis system, comprising:
   a) an electronic user interface having a device into which a user may enter commands;
   b) an electronic data acquisition module capable of capturing imagery data;
   c) an electronic display module for transmitting information to the user; and
   d) a data analysis and reporting unit containing program instructions and memory that:
      (1) using the display module, prompt the user with queries for personal health information of a patient, and transmit instructions to the user for positioning of the patient relative to the data acquisition module to capture an image of an area of dermatological interest on the patient's body,
      (2) analyze the images captured by the data acquisition module along with the personal health information of the patient,
      (3) based on the analysis, develop a primary diagnosis for the patient of a physiological abnormality or disorder from a cause selected from the group consisting of dietary/nutritional deficiencies, blood toxicity/poisoning, contagious or infectious diseases, exposure to fungal infections, or exposure to parasitical infections, injury, drug and alcohol abuse, drug interactions/reactions, exposure to an irritant or caustic substance, or exposure to at least one of hazardous microorganisms, hazardous chemicals, poisons, environmental pollutants, infestations, or nuclear/biological/chemical contamination, and that can manifest in the form of a skin condition,
  (4) select a primary treatment for the physiological abnormality or disorder other than the selection of a topical dermatological product based on the diagnosis,
  (5) create a monitoring program for following up with the patient on the efficacy of the primary treatment of the physiological abnormality or disorder, and
  (6) transmit the primary diagnosis, primary treatment, and monitoring program to the user.

2. The system of claim 1, wherein the electronic data acquisition module includes at least one of the following: a stationary digital image scanner, a portable digital image scanner, and a digital camera capable of capturing either photographic or video images.

3. The system of claim 1, wherein the electronic data acquisition module further acquires variances in fluorescence landscapes using a fluorescence spectroscope.

4. The system of claim 1, wherein the electronic data acquisition module further acquires digital radiometric images using an infrared (IR) imager.

5. The system of claim 1, further including a test and measurement unit that acquires sensory data from the patient using a breath analyzer, wherein the data analysis and reporting unit incorporates the sensory data when developing the diagnosis.

6. The system of claim 1, further including a test and measurement unit capable of importing external laboratory results of the patient, wherein the data analysis and reporting unit incorporates the laboratory results when developing the diagnosis.

7. The system of claim 1, wherein the data analysis and reporting unit further contains program instructions that interactively prompts the user with queries for personal health information including psychological and behavioral characteristics of a patient by customizing subsequent queries based on responses from previous queries.

8. The system of claim 7, wherein the data analysis and reporting unit prompts the user with queries for demographic information, including queries concerning at least one of the following: race, ethnicity, educational level, occupation, sexual preference, marital status, children, religion, recreational activities.

9. The system of claim 1, wherein the data analysis and reporting unit further contains program instructions that interactively transmit instructions to the user for positioning of the patient relative to the data acquisition module to capture images of an area of dermatological interest on the patient's body by analyzing responses to patient queries.

10. The system of claim 1, wherein the data analysis and reporting unit further contains program instructions for primary treatment effectiveness monitoring sensitized to alternative diagnoses and treatments so that certain responses to the primary treatment may be correlated to the corresponding response characteristics of an alternative diagnosis.

11. The system of claim 10, wherein if the primary treatment effectiveness monitoring detects evidence that the primary treatment is ineffective against the primary diagnosis and/or if the patient's response to the primary treatment corresponds to one or more unique response characteristics associated with an alternative diagnosis, the primary diagnosis is reassessed and the system transmits an alternative diagnosis, treatment, and monitoring program to the user.

12. The system of claim 1, further including:
  (e) a centralized data analysis and reporting unit that interacts with a network of remotely located user interface and display units including elements (a)-(c) and updates reference materials to keep them current.

13. The system of claim 12, wherein a number of the remotely located user interface and display units are portable.

14. A derma diagnostic and automated data analysis system, comprising:
  (a) an electronic user interface having a device into which a user may enter commands;
  (b) an electronic data acquisition module capable of capturing imagery data;
  (c) an electronic display module for transmitting information to a user; and
  (d) a data analysis and reporting unit containing program instructions and memory that:
    (1) using the display module, transmit instructions to the user for positioning of the patient relative to the data acquisition module to capture an image of an area of dermatological interest on the patient's body,
    (2) analyze the images captured by the data acquisition module,
    (3) based on the analysis, develop a primary and secondary diagnosis for the patient of a physiological abnormality or disorder from a cause selected from the group consisting of dietary/nutritional deficiencies, blood toxicity/poisoning, contagious or infectious diseases, exposure to fungal infections, or exposure to parasitical infections, injury, drug and alcohol abuse, drug interactions/reactions, exposure to an irritant or caustic substance, or exposure to at least one of hazardous microorganisms, hazardous chemicals, poisons, environmental pollutants, infestations, or nuclear/biological/chemical contamination, and that can manifest in the form of a skin condition,
    (4) select a primary treatment other than the selection of a topical dermatological product based on the primary diagnosis,
    (5) reconcile whether the primary treatment is compatible with the secondary diagnosis,
    (6) evaluate the relative probabilities of the primary and secondary diagnosis,
    (7) determine patient advice selected from either the primary treatment or instructions for further testing and evaluation if the primary treatment is incompatible with the secondary diagnosis and only marginally more probable than the secondary diagnosis, and
    (8) transmit patient advice to the user.

15. The system of claim 14, wherein the data analysis and reporting unit further contains program instructions for primary treatment effectiveness monitoring sensitized to the secondary diagnosis so that certain responses to the primary treatment may be correlated to the corresponding response characteristics of the secondary diagnosis.

16. The system of claim 15, wherein if the primary treatment effectiveness monitoring detects evidence that the primary treatment is ineffective against the primary diagnosis and/or if the patient's response to the primary treatment corresponds to one or more unique response characteristics associated with the secondary diagnosis, the primary diagnosis is reassessed and the system transmits the secondary diagnosis and a corresponding treatment and monitoring program to the user.

17. The system of claim 14, wherein the data analysis and reporting unit contains program instructions for updating programs to prescribe at least one secondary treatment when the primary treatment causes adverse reactions and/or is ineffective.

18. The system of claim 14, wherein the data analysis and reporting unit contains program instructions for monitoring and analyzing user interface inputs to detect the occurrence of conditions in unusual numbers, patterns or trends that are caused by certain nuclear, biological and/or chemical agents.

19. The system of claim 14, further including a test and measurement unit capable of importing external laboratory results of the patient, wherein the data analysis and reporting unit incorporates the laboratory results when developing the diagnosis.

20. The system of claim 14, wherein the data analysis and reporting unit further contains program instructions that interactively prompts the user with queries for personal health information including psychological and behavioral characteristics of a patient by customizing subsequent queries based on responses from previous queries.

21. The system of claim 14, wherein the data analysis and reporting unit further contains program instructions that interactively transmit instructions to the user for positioning of the patient relative to the data acquisition module to capture images of an area of dermatological interest on the patient's body by analyzing responses to patient queries.

22. The system of claim 14, further including:
(e) a centralized data analysis and reporting unit that interacts with a network of remotely located user interface and display units including elements (a)-(c) and updates reference materials to keep them current.

23. The system of claim 22, wherein a number of the remotely located user interface and display units are portable.

24. The system of claim 14, wherein the electronic data acquisition module further includes at least one of the following:
an ultraviolet emitter and detector, and
an infrared emitter and detector.

25. A derma diagnostic and automated data analysis system, comprising:
(a) an electronic user interface having a device into which a user may enter commands;
(b) an electronic data acquisition module for capturing visual imagery data;
(c) an electronic display module for transmitting information to a user; and
(d) a data analysis and reporting unit containing program instructions and memory that:
(1) using the display module, transmit instructions to the user for positioning of the patient relative to the data acquisition module to capture a visual image of an area of dermatological interest on the patient's body,
(2) analyze the images captured by the data acquisition module;
(3) based on the analysis, develop a primary diagnosis for the patient of a physiological abnormality or disorder from a cause selected from the group consisting of dietary/nutritional deficiencies, blood toxicity/poisoning, contagious or infectious diseases, exposure to fungal infections, or exposure to parasitical infections, injury, drug and alcohol abuse, drug interactions/reactions, exposure to an irritant or caustic substance, or exposure to at least one of hazardous microorganisms, hazardous chemicals, poisons, environmental pollutants, infestations, or nuclear/biological/chemical contamination, and that can manifest in the form of a skin condition,
(4) select a primary treatment for the physiological abnormality or disorder other than the selection of a topical dermatological product based on the primary diagnosis, and
(5) transmit the primary diagnosis and treatment to the user,
(f) a centralized data analysis and reporting unit that interacts with a network of remotely located user interface and display units including elements (a)-(c) and updates reference materials to keep them current.

26. The system of claim 25, wherein a number of the remotely located user interface and display units are portable.

27. The system of claim 25, further including a test and measurement unit that acquires sensory data from the patient using a breath analyzer.

28. The system of claim 25, further including a test and measurement unit capable of importing external laboratory results of the patient, wherein the data analysis and reporting unit incorporates the laboratory results when developing the diagnosis.

29. The system of claim 25, wherein the data analysis and reporting unit further contains program instructions that interactively prompts the user with queries for personal health information including psychological and behavioral characteristics of a patient by customizing subsequent queries based on responses from previous queries.

30. The system of claim 29, wherein the data analysis and reporting unit prompts the user with queries for demographic information, including queries concerning at least one of the following: race, ethnicity, educational level, occupation, sexual preference, marital status, children, religion, recreational activities.

31. The system of claim 25, wherein the data analysis and reporting unit further contains program instructions that interactively transmit instructions to the user for positioning of the patient relative to the data acquisition module to capture visual images of an area of dermatological interest on the patient's body by analyzing responses to patient queries.

32. The system of claim 25, wherein the data analysis and reporting unit further contains program instructions for primary treatment effectiveness monitoring sensitized to alternative diagnoses and treatments so that certain responses to the primary treatment may be correlated to the corresponding response characteristics of an alternative diagnosis.

33. The system of claim 32, wherein if the primary treatment effectiveness monitoring detects evidence that the primary treatment is ineffective against the primary diagnosis and/or if the patient's response to the primary treatment corresponds to one or more unique response characteristics associated with an alternative diagnosis, the primary diagnosis is reassessed and the system transmits an alternative diagnosis, treatment, and monitoring program to the user.

34. The system of claim 25, wherein the electronic data acquisition module further includes one of the following:
an ultraviolet emitter and detector, and
an infrared emitter and detector.

\* \* \* \* \*